(12) United States Patent
Buschmann et al.

(10) Patent No.: US 6,344,558 B1
(45) Date of Patent: Feb. 5, 2002

(54) 1-PHENYL-3-DIMETHYLAMINOPROPANE COMPOUNDS WITH A PHARMACOLOGICAL EFFECT

(75) Inventors: Helmut Buschmann, Aachen; Wolfgang Strassburger, Wuerselen; Elmar Friderichs, Stolberg, all of (DE)

(73) Assignee: Gruenthal GmbH, Aachen (DE)

( * ) Notice: Subject to any disclaimer, the term of this patent is extended or adjusted under 35 U.S.C. 154(b) by 0 days.

(21) Appl. No.: 09/838,192

(22) Filed: Apr. 20, 2001

Related U.S. Application Data

(62) Division of application No. 08/466,911, filed on Jun. 6, 1995, now Pat. No. 6,248,737.

(30) Foreign Application Priority Data

Jul. 23, 1994 (DE) .......................................... 44 26 245

(51) Int. Cl.[7] ............................................ C07C 217/62
(52) U.S. Cl. ..................... 544/86; 549/398; 558/190; 558/273; 560/32; 560/37; 560/66; 560/250; 560/252; 564/355; 564/356; 564/374; 564/440; 564/442; 564/443
(58) Field of Search ........................... 544/86; 549/398; 558/190, 273; 560/32, 37, 66, 250, 252; 564/355, 356, 374, 440, 442, 443

(56) References Cited

U.S. PATENT DOCUMENTS

| | | | | |
|---|---|---|---|---|
| 4,285,961 A | * | 8/1981 | Prucher et al. | 424/273 R |
| 5,310,756 A | * | 5/1994 | Jakobsen et al. | 514/524 |
| 5,811,582 A | * | 9/1998 | Buschmann et al. | 564/355 |
| 5,981,599 A | * | 11/1999 | Moe et al. | 514/654 |
| 6,001,884 A | * | 12/1999 | Nemeth et al. | 514/699 |
| 6,011,068 A | * | 1/2000 | Nemeth et al. | 514/654 |
| 6,017,965 A | * | 1/2000 | Mueller et al. | 514/649 |
| 6,022,894 A | * | 2/2000 | Del Mar et al. | 514/524 |
| 6,031,003 A | * | 2/2000 | Nemeth et al. | 514/579 |
| 6,051,610 A | * | 4/2000 | Mueller et al. | 514/628 |
| 6,071,970 A | * | 6/2000 | Mueller et al. | 514/648 |

FOREIGN PATENT DOCUMENTS

| | | | |
|---|---|---|---|
| DE | 1051281 | * | 2/1959 |
| DE | 2412798 | * | 9/1974 |
| DE | 124521 | | 3/1977 |
| DE | 3242922 | | 5/1984 |
| EP | 176049 | | 4/1986 |
| WO | WO 95/21612 | * | 8/1995 |

OTHER PUBLICATIONS

Tramatoni, "Advances in the Chemistry of Mannich Bases", *Synthesis*, 1973, pp. 703–775.
*J. Am. Chem. Soc.*, 74, p. 1316 (1952).
*Chem. Abstr.*, 63, p. 6912e (1965).
Olofsson et al., "Value of the Vinyloxycarbonyl Unit in Hydroxyl protection: Application of the Synthesis of Nalorphine", *Tetrahedron Letters*, No. 18, 1977, pp. 1571–1574.

Welch et al., "Reduction of Aryl Diethyl Phosphates with Titanium Metal: A method for Deoxygenation of Phenols", *J. Org. Chem.*, 43, pp. 4797–4799 (1978).
Ditter et al., "Acetaminophen Prodrugs I", *J. Pharm. Sci.*, 57, pp. 774–780 (1968).
Thorberg et al., "Carbamate Ester Derivatives as Potential Prodrugs of the Presynaptic Dopamine Autoreceptor Agonist . . .", *J. Med. Chem.*, 30, pp. 2008–2012 (1987).
Bundgaard et al., "A Novel Solution–Stable, Water Soluble Prodrug Type for Drugs Containing a Hydroxyl or an HG–Acidic Group", *J. Med. Chem.*, 32, pp. 2503–2507 (1989).
Raffa et al., "Opioid and Nonopioid Components Independently Contribute to the Mechanism of Action of Tramadol . . .", *J. Pharmacol. Exptl. Ther.*, 260. pp. 275–85 (1992).
Burwell, "The Cleavage of Ethers", *Chem. Rev.*, 54, pp. 615–85 (1954).
Winterfeldt, "Applications of Diisobutylaluminium Hydride (DIBAH) and Triisobutylaluminium (TIBA) as Reducing Agents in Organic Synthesis", *Synthesis*, 1975, pp. 617–630.
Bundgaard, "Novel Chemical Approaches in Prodrug Design", *Drugs of the Future*, 16, pp. 443–458, (1991).
*Organic Reactions*, 35, Chapter 3, pp. 513–633 (1988).
Goodman & Gilman, *The Pharmacological Basis of Therapeutics*, Pergamon Press, New York (1990).
Potti et al., "Use of 3–Azabicyclo [3,2,1]Octane in the Mannich Reaction", *J. Pharm. Sci.*, 57, pp. 1487–93– (1968).
Spassov et al., "Stereochemistry of Diastereomeric 3–Dialkylaminopropanols and O–Derivatives", *J. Prakt. Chem.*, 323, pp. 793–800 (1981).
Parimoo et al., "New Compounds: Some Potential Chemotherapeutic Agents Derived from Aralkyl Ketones", *J. Pharm. Sci.*, 59, pp. 1038–1041 (1970).
Raffa et al., "Complementary and Synergistic Antinociceptive Interaction between the Enantiomers of Tramadol", *J. Pharmacol. Exptl. Ther.*, 267, pp. 331–340 (1993).
*Chem. Abstr.*, 54, 2093c (1960).

* cited by examiner

*Primary Examiner*—Richard L. Raymond
(74) *Attorney, Agent, or Firm*—Crowell & Moring LLP

(57) ABSTRACT

1-phenyl-3-dimethylaminopropane compounds corresponding to the formula I

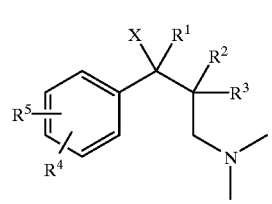

a method of preparing them, and the use of these substances as analgesic active ingredients in pharmaceutical compositions.

8 Claims, No Drawings

1-PHENYL-3-DIMETHYLAMINOPROPANE COMPOUNDS WITH A PHARMACOLOGICAL EFFECT

This application is a division of application Ser. No. 08/466,911, filed Jun. 6, 1995, now U.S. Pat. No. 6,248,737.

BACKGROUND OF THE INVENTION

The present invention relates to 1-phenyl-3-dimethylaminopropane compounds, to a method of preparing them, and to the use of these substances as pharmaceutical active ingredients.

The treatment of chronic and non-chronic pain situations is of great importance in medicine. This is reflected in the large number of publications. Thus, for example, 1-naphthyl-3-aminopropane-1-ols with an analgesic-narcotic effect are known from EP 176 049. Secondary and tertiary alcohols with γ-amino groups are described in *J. Pharm. Sci.* 59, 1038 (1970) and in *J. Prakt. Chem.* 323, 793 (1981); phenyl-dimethylaminopropanols containing a para-substituted phenyl radical are described in *Chem. Abstr.* 54, 20936c (1960) and in *Chem. Abstr.* 63, 6912e (1965). These compounds also possess analgesic properties. In contrast, the 3-dimethylaminopropan-1-ols containing 2-phenyl radicals described in DE 32 42 922 have an antidepressant effect. The 1-phenyl-propan-1-ols described in *J. Pharm. Sci.* 57, 1487 (1968) have different pharmacological effects depending on the γ-aza ring.

Opioids have been used for many years as analgesics for the treatment of pain, although they give rise to a series of side effects, for example addiction and dependency, respiratory depression, gastrointestinal inhibition and obstipation. They can therefore only be given over an extended period of time or in higher doses subject to special precautionary measures such as special prescription regulations (Goodman, Gilman in *"The Pharmacological Basis of Therapeutics"*, Pergamon Press, New York (1990)).

Tramadol hydrochloride—(1RS,2RS)-2-[(dimethylamino)methyl]-1-(3-methoxyphenyl)cyclohexanol hydrochloride—assumes a special position amongst centrally-acting analgesics, since this active ingredient gives rise to a pronounced inhibition of pain without the side effects which are known for opioids (*J. Pharmacol. Exptl. Ther.*4 267, 331 (1993)). Tramadol is a racemate and consists of identical amounts of (+) and (−) enantiomer. In vivo the active ingredient forms the metabolite O-desmethyl-tramadol, which is likewise present as a mixture of enantiomers. Investigations have shown that both the enantiomers of tramadol and the enantiomers of tramadol metabolites contribute to the analgesic effect (*J. Pharmacol. Exp. Ther.* 260, 275 (1992)).

SUMMARY OF THE INVENTION

The underlying object of the present invention was to provide substances with an analgesic effect, which are suitable for the treatment of severe pain without giving rise to the side effects which are typical of opioids.

A further object was to provide analgesic substances which do not exhibit the side effects, for example nausea and vomiting, which occur during treatment with tramadol in some cases.

It has been found that these stringent requirements are fulfilled by certain 1-phenyl-3-dimethylaminopropane compounds. These substances are characterized by a pronounced analgesic effect which is significantly enhanced compared with that of tramadol.

The present invention accordingly relates to 1-phenyl-3-dimethylaminopropane compounds of formula I

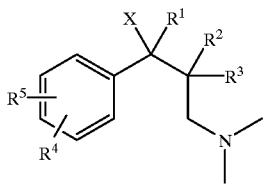

in which

X represents OH, F, Cl, H or an OCOR$^6$ group in which R$^6$ is a C$_{1-3}$-alkyl group;

R$^1$ is a C$_{1-4}$-alkyl group;

R$^2$ represents H or a C$_{1-4}$-alkyl group and R$^3$ represents H or a straight chain C$_{1-4}$-alkyl group, or R$^2$ and R$^3$ together constitute a C$_{4-7}$ cycloalkyl radical, and if R$^5$ is H, R$^4$ represents meta-O—Z, where Z is H, C$_{1-4}$-alkyl, PO(OC$_{1-4}$-alkyl)$_2$, CO(OC$_{1-5}$-alkyl), CONH—C$_6$H$_4$—(C$_{1-3}$-alkyl) or CO—C$_6$H$_4$—R$^7$, wherein R$^7$ is ortho-OCOC$_{1-3}$-alkyl or meta- or para-CH$_2$N(R$^8$)$_2$, where R$^8$ is C$_{1-4}$-alkyl or 4-morpholino, or R$^4$ represents meta-S—C$_{1-3}$-alkyl, meta-Cl, meta-F or meta-CR$^9$R$^{10}$R$^{11}$, ortho-OH, ortho-O—C$_{2-3}$-$_3$-alkyl, para-F or para-CR$^9$R$^{10}$R$^{11}$, where R$^9$, R$^{10}$ and R$^{11}$ represent H or F, or if R$^5$ represents Cl, F, OH or O—C$_{1-3}$-alkyl in the para-position, R$^4$ represents Cl, F, OH or O—C$_{1-3}$-alkyl in the meta-position, or R$^4$ and R$^5$ together represent 3,4-OCH=CH$_2$— or 3,4-OCH=CHO—, as diastereoisomers or enantiomers in the form of free bases or salts of physiologically acceptable acids.

1-phenyl-3-dimethylaminopropane compounds of formula I are preferred in which X constitutes OH, F, Cl or H; R$^1$ represents a C$_{1-4}$-alkyl group; R$^2$ represents H or CH$_3$, and R$^3$ represents H or CH$_3$, and if R$^5$ is H, R$^4$ represents OC$_{1-3}$-alkyl, —OH, —S—C$_{1-3}$-alkyl, F, Cl, CH$_3$, —CF$_2$H or —CF$_3$ in the meta-position, or para-CF$_3$, or if R5 is a para-Cl or para-F, R$^4$ represents meta-Cl or meta-F, or R$^4$ and R$^5$ together represent 3,4-OCH=CH2—.

1-phenyl-3-dimethylaminopropane compounds of formula I are particularly preferred in which the R$^2$ and R$^3$ radicals have different meanings, in the form of their diastereoisomers of configuration Ia

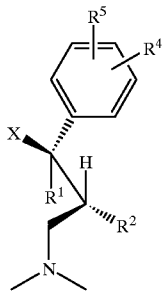

The present invention also relates to a method of preparing 1-phenyl-3-dimethylaminopropane compounds of formula I, in which the variable X represents OH, which is characterized in that a β-dimethylaminoketone of formula II

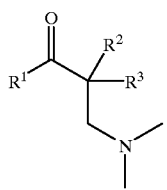

is reacted with an organometallic compound of formula III

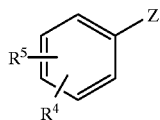

in which Z represents MgCl, MgBr, MgI or Li, to form a compound of formula I in which X represents OH.

The reaction of a β-dimethylaminoketone with a Grignard reagent of formula III, in which Z represents MgCl, MgBr or MgI, or with an organolithium compound of formula III, can be carried out in an aliphatic ether, for example diethyl ether and/or tetrahydrofuran, at temperatures between −70° C. and +60° C. Organolithium compounds of formula II can be obtained by the replacement of halogen by lithium, for example, by reacting a compound of formula III, in which Z represents Cl, Br or I, with a solution of n-butyllithium in n-hexane. β-dimethylaminoketones of formula II can be obtained from ketones of general formula IV

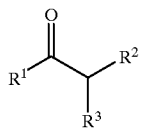

by reaction with dimethylamine hydrochloride and formaldehyde in glacial acetic acid or in a $C_{1-4}$-alkyl alcohol or by reaction with dimethylammonium ethylene chloride in acetonitrile using acetyl chloride as a catalyst (*Synthesis* 1973, 703).

Upon reaction of a β-dimethylaminoketone of formula II, in which the variables $R^2$ and $R^3$ have different meanings, with an organometallic compound of formula III, 1-phenyl-3-dimethylaminopropane compounds of formula I are obtained having the relative configuration of formula Ia

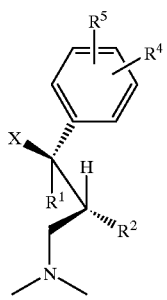

in which the X and the dimethylamino group are disposed threo in relation to each other. In contrast, if the reaction for the preparation of 1-phenyl-1-hydroxy-3-aminopropanes were carried out according to the method disclosed in DD 124 521, i.e. if β-aminoketones corresponding to the formula V

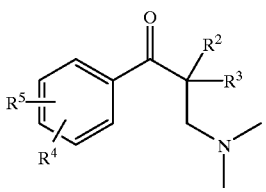

were reacted with an alkyl Grignard reagent $R^1$MgHal, this would result in compounds with the relative configuration Ib

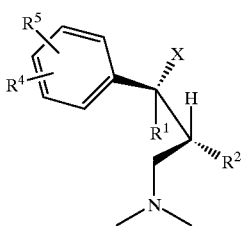

in which the OH group and the dimethylamino radical are disposed erythro in relation to each other.

1-phenyl-3-dimethylaminopropane compounds of formula I, in which $R^4$ and/or $R^5$ constitute the OH group, can be prepared from the corresponding 1-(4(5)-methoxyphenyl)-3-dimethylaminopropanol compounds by selective ether cleavage with diisobutylaluminium hydride in an aromatic hydrocarbon, for example toluene, at a temperature between 60 and 130° C. (*Synthesis* 1975, 617).

The present invention also relates to a method of preparing 1-phenyl-3-dimethylaminopropane compounds of formula I, in which X represents H, which is characterized in that a compound of formula I, in which X represents Cl, is reacted with zinc borohydride, zinc cyanoborohydride and/or tin cyanoborohydride.

The reaction is usually conducted in a solvent, for example diethyl ether and/or tetrahydrofuran, at a temperature between 0° C. and 30° C.

Compounds of formula I, in which X is H and R and/or $R^5$ constitute the OH group, can be prepared from the corresponding methoxyphenyl compounds by heating them for several hours with concentrated hydrobromic acid (*Chem. Rev.* 54, 615 (1954); *J. Am. Chem. Soc.* 74, 1316 (1952)).

The present invention further relates to a method of preparing 1-phenyl-3-dimethylaminopropane compounds of formula I, where X represents F, which is characterized in that a compound of formula I, in which X represents OH, is reacted with dimethylaminosulfur trifluoride in a solvent.

Suitable solvents include dichloromethane, 1,1,2-trichloroethane and/or toluene. The reaction is usually conducted at a temperature between −50° C. and +30° C. (*Org. React.* 35, 513 (1988)). If a compound of formula I with X=OH is used in which $R^4$ and/or $R^5$ constitute OH groups, these OH groups must be protected before reaction with the fluorine compound, for example by reaction with benzoyl chloride.

The present invention also relates to a method of preparing 1-phenyl-3-dimethylaminopropane compounds of formula I, in which X represents Cl, which is characterized in that a compound of formula I, in which X represents OH, is reacted with thionyl chloride.

The reaction is usually conducted in the absence of solvent at a temperature between 0° C. and 20° C. Replacement of OH by Cl is effected while maintaining the configuration.

The present invention also relates to a method of preparing 1-phenyl-3-dimethylaminopropane compounds of formula I, in which X represents an $OCOR^6$ group where $R^6$ is a $C_{1-3}$-alkyl, which is characterized in that a compound of formula I, in which X represents OH, is reacted with an acid chloride Cl—$COOR^6$.

The reaction is preferably conducted in a solvent, for example dichloromethane, toluene and/or tetrahydrofuran, at a temperature between −10° C. and +30° C.

1-phenyl-3-dimethylaminopropane compounds of formula I, in which $R^5$ is H and $R^4$ is a meta-phosphate group, meta-carbonate group, meta-carbamate group or meta-carboxylate group, can be obtained by the reaction of the corresponding 1-(3-hydroxyphenyl)-3-dimethylaminopropane compounds of formula I in the form of their alkali salts with an alkali salt of a dialkyl chlorophosphate, with an alkyl chloroformate, with an aryl isocyanate or with a carboxylic acid chloride. These reactions are usually conducted in a solvent, for example toluene, dichloromethane, diethyl ether and/or tetrahydrofuran, at temperatures between −15° C. and +110° C. (*Drugs of the Future* 16, 443 (1991); *J. Med. Chem.* 30, 2008 (1987) and 32, 2503 (1989); *J. Org. Chem.* 43, 4797 (1978); *Tetrahedron Lett.* 1977, 1571; *J. Pharm. Sci.* 57, 774 (1968)).

The compounds of formula I can be converted in a known manner into their salts with physiologically acceptable acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably effected in a solvent, for example diethyl ether, diisopropyl ether, alkyl acetates, acetone and/or 2-butanone. Moreover, trimethylchlorosilane in aqueous solution is suitable for the preparation of hydrochlorides.

1-phenyl-3-dimethylaminopropane compounds of formula I are toxicologically harmless, so that they are suitable as pharmaceutical active ingredients in drugs.

Accordingly, the present invention also relates to the use of a 1-phenyl-3-dimethylaminopropane compound of formula I as a pharmaceutical active ingredient. Compounds of formula I are preferably used for the treatment of pain.

In addition to at least one 1-phenyl-3-dimethylaminopropane compound of formula I, the analgesics according to the invention may contain carriers, fillers, solvents, diluents, colorants and/or binders. The selection of auxiliary substances and of the amounts of the same to be used depends on whether the drug is to be administered orally, intravenously, intraperitoneally, intradermally, intramuscularly, intranasally or locally, for example for infections of the skin, of the mucous membranes or of the eye. Preparations in the form of tablets, dragees, capsules, granules, drops, liquids and syrups are suitable for oral application. Solutions, suspensions, readily reconstitutable dry preparations, and sprays are suitable for parenteral, topical and inhalative applications. Compounds of formula I according to the invention in a deposit in dissolved form or in a patch, optionally with the addition of a skin penetration promoter, are suitable preparations for percutaneous application. Forms of preparations which can be administered orally or percutaneously may effect delayed release of the compounds of formula I according to the invention.

The amount of active ingredient to be administered to patients varies depending on the patient's weight, on the manner of administration, the indication and the degree of severity of the illness. 50 to 500 mg/kg of at least one 1-phenyl-3-dimethylaminopropane compound of formula I are usually administered.

EXAMPLES

The yields of the compounds prepared have not been optimised.

All temperatures are uncorrected.

Unless otherwise indicated, petroleum ether with a boiling point of 50–70° C. was used. The term "ether" denotes diethyl ether.

Silica gel 60 (0.040–0.063 mm) manufactured by E. Merck, Darmstadt, was used as the stationary phase for column chromatography.

Thin layer chromatography investigations were conducted using prefabricated silica gel 60 F 254 HPTLC plates manufactured by E. Merck, Darmstadt.

Racemate separation was effected on a Chiracel OD column.

The mixture ratios of the mobile phases for all chromatographic investigations are expressed as volume/volume.

RT denotes room temperature; m.p. denotes melting point.

Example 1

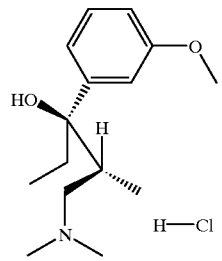

(2RS,3RS)-1-dimethylamino-3-(3-methoxyphenyl)-2-methylpentan-3-ol hydrochloride(1)

207.63 g (1.11 mole) 3-bromoanisole dissolved in 400 ml dry tetrahydrofuran were added drop-wise to 26.99 g (1.11 mole) magnesium turnings in 150 ml dry tetrahydrofuran so that the reaction mixture boiled gently. After the addition of 3-bromo-anisole was complete the mixture was heated under reflux for one hour and thereafter was cooled to 5–10° C. 128.30 g (0.89 mole) 1-dimethylamino-2-methylpentan-3-one dissolved in 400 ml tetrahydrofuran were added at this temperature. The reaction mixture was allowed to stand overnight and then cooled again to 5–10° C. The Grignard solution was decomposed by the addition of 300 ml of 20% ammonium chloride solution. The reaction mixture was diluted with 400 ml ether, the organic phase was separated off and the aqueous phase was extracted twice with 250 ml ether. The combined organic phases were dried over sodium sulphate. After removing the solvent by distillation, the residue (212 g) was taken up in 3200 ml 2-butanone and added to 120.60 g (1.11 mole) trimethylchlorosilane and 20 ml water. 121.5 g of hydrochloride (1) (38% theoretical) with a melting point of 198–199° C. crystallised out at 4–5° C.

Example 2

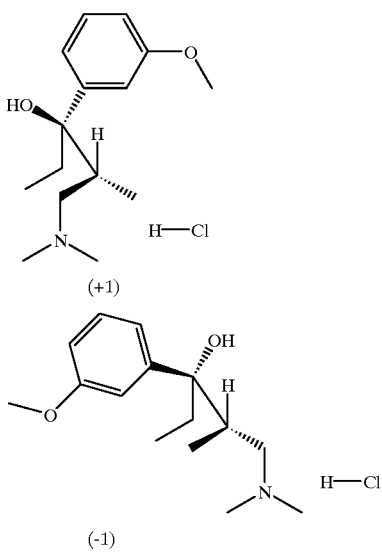

Enantiomers of (1)

(−)-(2S,3S)-1-dimethylamino-3-(3-methoxyphenyl)-2-methylpentan-3-ol hydrochloride(−1)
and
(+)-(2R, 3R)-1-dimethylamino-3-(3-methoxyphenyl)-2-methylpentan-3-ol hydrochloride (+1)

The base was released from (1) with dichloromethane/sodium hydroxide solution. After drying the solution dichloromethane was distilled off under vacuum. The racemate was then separated on the chiral HPLC column. The hydrochlorides, which had a melting point of 150–151° C., were prepared from the enantiomers obtained by reaction with trimethylchlorosilane/water in 2-butanone.

(−1): yield: 42% theoretical
$[\alpha]_{D\,RT} = -31.8°$ (c=0.99; methanol)
(+1): yield: 41% theoretical
$[\alpha]_{D\,RT} = +33.0°$ (c=0.96; methanol)

Example 3

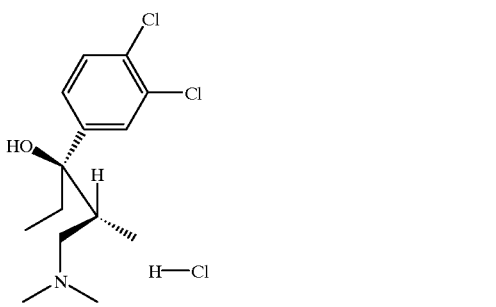

(2RS,3RS)-3-(3,4-dichlorophenyl)-1-dimethylamino-2-methylpentan-3-ol hydrochloride (2)

39 g of crude mixture were prepared analogously to Example 1 from 15 g (105 mmole) 1-dimethylamino-2-methylpentan-3-one, 35.5 g (157 mmole) 4-bromo-1,2-dichlorobenzene and 3.8 g (157 mmole) magnesium turnings. This mixture was introduced on to a 7×40 cm column packed with silica gel and eluted with 4:1 ethyl acetate/methanol. 14.9 g of base were obtained, from which 11.2 g of hydrochloride (2) (31% theoretical) with a melting point of 183–184° C. were obtained with trimethylchlorosilane/water in 2-butanone/diisopropyl ether.

Example 4

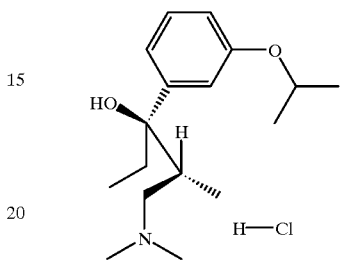

(2RS,3RS)-3-(3-isopropoxyphenyl)-1-dimethylamino-2-methylpentan-3-ol hydrochloride (3)

25 g of crude mixture were prepared analogously to Example 1 from 14.3 g (100 mmole) 1-dimethylamino-2-methylpentan-3-one, 20.0 g (157 mmole) 1-bromo-3-isopropoxybenzene and 2.79 g (115 mmole) magnesium turnings. This mixture was introduced on to a 7×40 cm column packed with silica gel and eluted with 15:1 ethyl acetate/methanol. 9.0 g of base were obtained, from which 8.3 g of hydrochloride (3) (26% theoretical) with a melting point of 133–134° C. were obtained with trimethylchlorosilane/water in 2-butanone.

Example 5

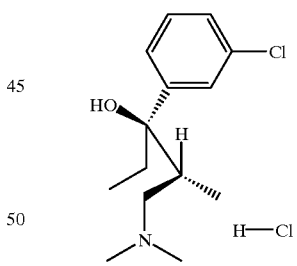

(2RS,3RS)-3-(3-chlorophenyl)-1-dimethylamino-2-methylpentan-3-ol hydrochloride (4)

63 g of crude mixture were obtained under the conditions cited for Example 1 from 38.0 g (270 mmole) 1-dimethylamino-2-methylpentan-3-one, 74.7 g (390 mmole) 1-bromo-3-chlorobenzene and 9.50 g (390 mmole) magnesium turnings. This mixture was introduced on to a 7×45 cm column packed with silica gel and eluted with 7:1 diisopropyl ether/methanol. 12.8 g of base were obtained, from which 10.8 g of hydrochloride (4) (14% theoretical) with a melting point of 160–162° C. were obtained with trimethylchlorosilane/water in 2-butanone/ether.

Example 6

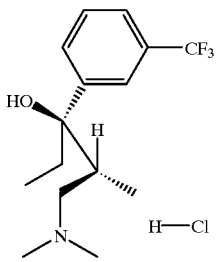

(2RS,3RS)-1-dimethylamino-2-methyl-3-(3-trifluoromethylphenyl)-pentan-3-ol hydrochloride(5)

21.2 g of crude mixture were obtained under the conditions cited for Example 1 from 14.3 g (100 mmole) 1-dimethylamino-2-methylpentan-3-one, 29.3 g (130 mmole) 1-bromo-3-trifluoromethylbenzene and 3.2 g (130 mmole) magnesium turnings. This mixture was introduced on to a 6×40 cm column packed with silica gel and eluted with 10:1 diisopropyl ether/methanol. 9.1 g of base were obtained, from which 7.8 g of hydrochloride (5) (18.5% theoretical) with a melting point of 189–190° C. was obtained with trimethylchlorosilane/water in 2-butanone.

Example 7

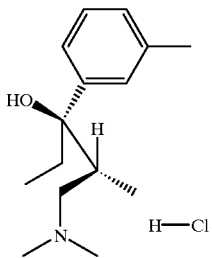

(2RS,3RS)-1-dimethylamino-2-methyl-3-(3-m-tolyl)-pentan-3-ol hydrochloride (6)

75 g of crude mixture were obtained as in Example 1 from 47.3 g (330 mmole) 1-dimethylamino-2-methylpentan-3-one, 64.6 g (400 mmole) 3-bromotoluene and 9.72 g (400 mmole) of magnesium turnings. This mixture was introduced on to a 7×50 cm column packed with silica gel and eluted with 7:1 diisopropyl ether/methanol. 24.3 g of base were obtained, from which 21.5 g of hydrochloride (6) (24% theoretical) with a melting point of 154–155° C. were obtained with trimethylchlorosilane/water in 2-butanone.

Example 8

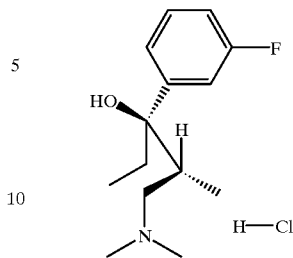

(2RS,3RS)-1-dimethylamino-3-(3-fluorophenyl)-2-methylpentan-3-ol hydrochloride (7)

70 g of crude mixture were obtained under the conditions cited for Example 1 from 54.0 g (380 mmole) 1-dimethylamino-2-methylpentan-3-one, 82.5 g (470 mmole) 1-bromo-3-fluorobenzene and 9.23 g (470 mmole) magnesium turnings. This mixture was introduced on to a 7×50 cm column packed with silica gel and eluted with 1:1 ethyl acetate/methanol. 13.0 g of base were obtained, from which 11.2 g of hydrochloride (7) (11.5% theoretical) with a melting point of 145–146° C. was obtained with trimethylchlorosilane/water in 2-butanone.

Example 9

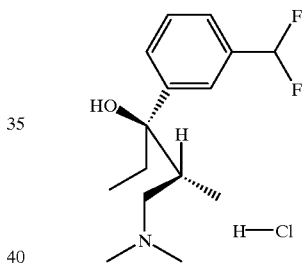

(2RS,3RS)-3-(3-difluoromethylphenyl)-1-dimethylamino-2-methylpentan-3-ol hydrochloride (8)

7.0 g (34 mmole) 1-bromo-3-difluoromethylbenzene, prepared from 3-bromobenzaldehyde and diethylaminosulphur trifluoride in dichloromethane according to Org. React. 35, 513 (1988) were dissolved in 110 ml of dry tetrahydrofuran and cooled to −75° C. After the addition of 21.12 ml (34 mmole) of a 1.6 molar solution of n-butyllithium in hexane the mixture was stirred for one hour at −75° C. 4.8 g (34 mmole) 1-dimethylamino-2-methylpentan-3-one dissolved in 15 ml of dry tetrahydrofuran were then added drop-wise. The reaction mixture was warmed to room temperature over 2.5 hours.

Work-up was effected by the dropwise addition of 65 ml of 5% hydrochloric acid with cooling in an ice bath, so that the internal temperature did not exceed 15° C. After phase separation the organic phase was extracted with 40 ml of 5% hydrochloric acid. The combined aqueous phases were washed twice with 50 ml ether. In order to release the base, the mixture was added to concentrated sodium hydroxide solution and extracted with dichloromethane. 7.8 g of crude product were obtained in this manner and was introduced on to a 7×40 cm column packed with silica gel. Elution with 1:1 ethyl acetate/methanol gave 4.89 g of base, from which 4.6 g of hydrochloride (8) (44% theoretical) with a melting point of 194–195° C. was obtained with trimethylchlorosilane/water in 2-butanone.

Example 10

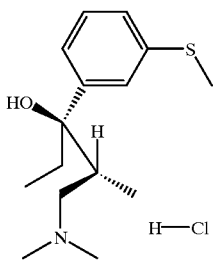

(2RS,3RS)-1-dimethylamino-2-methyl-3-(3-methylsulphanylphenyl)-pentan-3-ol hydrochloride (9)

38 g of crude mixture were obtained under the conditions cited for Example 1 from 17.6 g (123 mmole) 1-dimethylamino-2-methylpentan-3-one, 25.0 g (123 mmole) 1-bromo-3-methylsulphanylbenzene and 3.0 g (123 mmole) magnesium turnings. This mixture was introduced on to a 7×40 cm column packed with silica gel and eluted with 10:1 ethyl acetate/methanol. 8.35 g of base were obtained, from which 7.2 g of hydrochloride (9) (19% theoretical) with a melting point of 159–160° C. were obtained with trimethylchlorosilane/water in 2-butanone.

Example 11

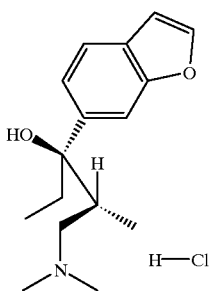

(2RS,3RS)-3-benzofuran-6yl-1-dimethylamino-2-methylpentan-3-ol hydrochloride(10)

3.45 g (18 mmole) 6-bromobenzofurane (prepared according to EP 355 827) and 6 ml 1,2-dibromoethane, dissolved in 60 ml dry ether, were added drop-wise over 1.5 hours to 2.12 g (87 mmole) magnesium turnings in 30 ml dry ether; after the addition the mixture was heated under reflux for 30 minutes. Thereafter, 2.5 g (18 mmole) 1-dimethylamino-2-methylpentan-3-one dissolved in 7.5 ml ether was added dropwise over 1.5 hours whilst cooling in an ice bath to maintain an internal temperature of 5–10° C. The reaction mixture was allowed to stand for 12 hours at room temperature, and was then cooled again to 5–10° C. and added to 35 ml of 20% aqueous ammonium chloride solution. After phase separation, the aqueous phase was extracted twice with 50 ml ether. The combined organic phases were dried over sodium sulphate. After removing the solvent by distillation the residue (3.9 g) was introduced on to a 5×16 cm column packed with silica gel. 0.95 g of base were obtained by elution with 7:1 diisopropyl ether/methanol, from which 0.82 g of hydrochloride (10) (15.5% theoretical) with a melting point of 162° C. were obtained with trimethylchlorosilane/water in ethyl acetate/2-butanone.

Example 12

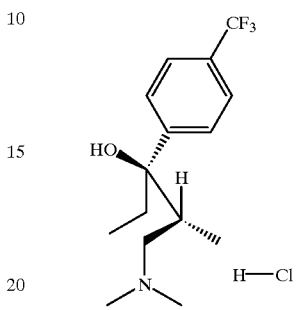

(2RS,3RS)-1-dimethylamino-2-methyl-3-(4-trifluoromethylphenyl)-pentan-3-ol hydrochloride (11)

44 g of crude mixture were obtained as in Example 1 from 20 g (140 mmole) 1-dimethylamino-2-methylpentan-3-one, 31.5 g (140 mmole) 1-bromo-4-trifluoromethylbenzene, 16.5 g (680 mmole) magnesium turnings and 47 ml 1,2-dibromoethane. This mixture was introduced on to a 7×50 cm column packed with silica gel and eluted with 5:1 ethyl acetate/methanol. 16.4 g of base were obtained, from which 12.3 g of hydrochloride (11) (27% theoretical) with a melting point of 170–171° C. were obtained with trimethylchlorosilane/water in 2-butanone.

Example 13

(3RS)-1-dimethylamino-3-(3-methoxyphenyl)-hexan-3-ol hydrochloride (12)

18.5 g of crude mixture were obtained as in Example 1 from 10 g (70 mmole) 1-dimethylamino-hexan-3-one, 18.7 g (100 mmole) 1-bromo-3-methoxybenzene and 2.3 g (100 mmole) magnesium turnings. This mixture was introduced on to a 6×50 cm column packed with silica gel and eluted with 1:1 ethyl acetate/methanol. 6.84 g of base were obtained, from which 6.15 g of hydrochloride (12) (32% theoretical) with a melting point of 179–180° C. were obtained with trimethylchlorosilane/water in 2-butanone.

Example 14

(3RS)-1-dimethylamino-3-(3-methoxyphenyl)-heptan-3-ol hydrochloride (13)

17.3 g of crude mixture were obtained as in Example 1 from 10 g (64 mmole) 1-dimethylamino-heptan-3-one, 15.9 g (157 mmole) 1-bromo-3-methoxybenzene and 2.06 g (85 mmole) magnesium turnings. This mixture was introduced on to a 6×40 cm column packed with silica gel and eluted with ethyl acetate. 5.4 g of base were obtained, from which 4.1 g of hydrochloride (13) (21% theoretical) with a melting point of 150° C. were obtained with trimethylchlorosilane/water in 2-butanone.

Example 15

(3RS)-1-dimethylamino-3-(3-methoxyphenyl)-4,4-dimethylpentan-3-ol hydrochloride(14)

37 g of crude mixture were obtained as in Example 1 from 18.6 g (118 mmole) 1-dimethylamino-4,4-dimethylpentan- 3-one, 28.4 g (152 mmole) 1-bromo-3-methoxybenzene and 3.7 g (152 mmole) magnesium turnings. This mixture was introduced on to a 7×40 cm column packed with silica gel and eluted with 5:1 ethyl acetate/methanol. 2.2 g of base were obtained, from which 1.8 g of hydrochloride (14) (5% theoretical) with a melting point of 213° C. were obtained with trimethylchlorosilane/water in 2-butanone.

Example 16

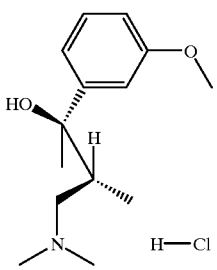

(2RS,3RS)-4-dimethylamino-2-(3-methoxyphenyl)-3-methylbutan-3-ol hydrochloride(15)

21 g of crude mixture were obtained as in Example 1 from 5.3 g (41 mmole) 4-dimethylamino-3-methylbutan-3-one, 23.0 g (123 mmole) 1-bromo-3-methoxybenzene and 3.0 g (123 mmole) magnesium turnings. This mixture was introduced on to a 4.5×27 cm column packed with silica gel and eluted with 4:1 ethyl acetate/methanol. 4.0 g of base were obtained, from which 3.6 g of hydrochloride (15) (32% theoretical) with a melting point of 124° C. were obtained with trimethylchlorosilane/water in 2-butanone.

Example 17

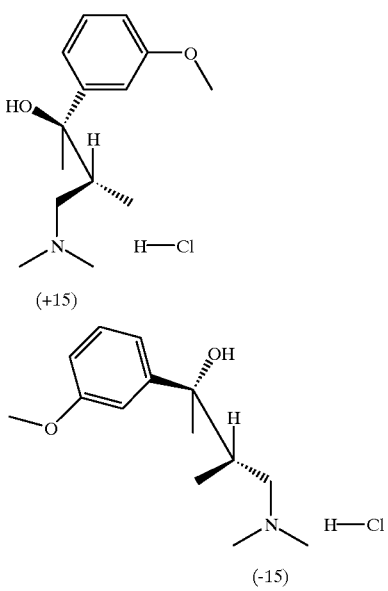

Enantiomers of (15)

(−)-(2S,3S)-4-dimethylamino-2-(3-methoxyphenyl)-3-methylbutan-3-ol hydrochloride (−15)

and (+)-(2R,3R)-4-dimethylamino-2-(3-methoxyphenyl)-3-methylbutan-3-ol hydrochloride(+15)

The base was released from hydrochloride (15), which was prepared as in Example 16, with dichloromethane/ sodium hydroxide solution. After drying and removal of dichloromethane by distillation, the racemate was then separated into the enantiomers on a chiral HPLC column. The hydrochlorides were obtained from the enantiomers with trimethylchlorosilane/water in 2-butanone.

(−15): yield: 41% theoretical m.p.: 117–118° C.

$[\alpha]_{D\ RT}=-38.6°$ (c=1.05; methanol)

(+15): yield: 41% theoretical m.p.: 118–119° C.

$[\alpha]_{D\ RT}=+41.0°$ (c=1.01; methanol)

Example 18

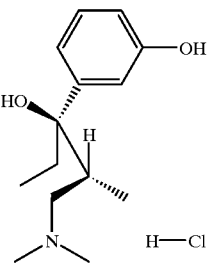

(2RS,3RS)-3-(3-dimethylamino-1-ethyl-1-hydroxy-2-methylpropyl)-phenol hydrochloride(16)

The base was released from compound (1), which was prepared as in Example 1, with dichloromethane/sodium hydroxide solution. After drying the solution, dichloromethane was removed by distillation. 4.3 g (17 mmole) of base were dissolved in 25 ml dry toluene and slowly added drop-wise to 71 ml (85 mmole) of a 1.2 molar solution of diisobutylaluminium hydride in toluene. When the addition was complete, the mixture was heated for 8 hours under reflux and then cooled to room temperature. The reaction mixture was diluted with 25 ml toluene. 9.4 ml ethanol followed by 9.4 ml water were added dropwise whilst cooling in an ice bath. After stirring for one hour whilst cooling in the ice bath the reaction mixture was freed from aluminium salts by filtration, and the residue was washed three times with 50 ml toluene in each case. Thereafter the combined organic phases were dried and toluene was removed by distillation. 3.95 g of hydrochloride (16) (85% theoretical) with a melting point of 213–214° C. were obtained from the base with aqueous hydrochloric acid solution in acetone.

Example 19

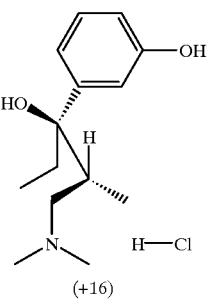

-continued

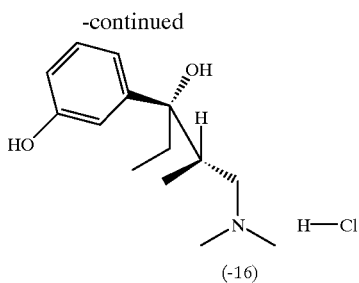

(-16)

Enantiomers of (16)

(−)(2S,3S)-3-(3-dimethylamino-1-ethyl-1-hydroxy-2-methylpropyl)-phenol hydrochloride(−16)

and (+)(2S,3S)-3-(3-dimethylamino-1-ethyl-1-hydroxy-2-methylpropyl)-phenol hydrochloride(+16)

The enantiomers (−16) and (+16) were prepared under the conditions cited in Example 2.

(−16): yield: 85% theoretical m.p.: 208–209° C.

$[\alpha]_{D\ RT} = -34.6°$ (c=0.98; methanol)

(+16): yield: 85% theoretical m.p.: 206–207° C.

$[\alpha]_{D\ RT} = +34.4°$ (c=1.06; methanol)

Example 20

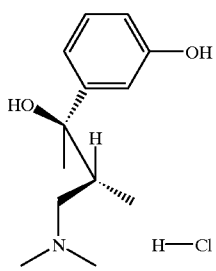

(1RS,2RS)-3-(3-dimethylamino-1-hydroxy-1,2-dimethylpropylphenol hydrochloride(17)

Compound (17) was prepared under the conditions cited in Example 18 starting from methoxy compound (15) which was obtained as in Example 16.

Yield: 85% theoretical m.p.: 232° C.

Example 21

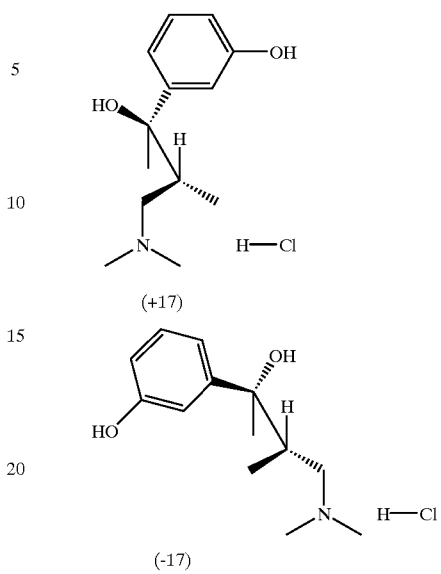

(+17)

(-17)

Enantiomers of (17)

(−)-(1S,2S)-3-(3-dimethylamino-1-hydroxy-1,2-dimethylpropyl)-phenol hydrochloride(−17)

and (+)-(1R,2R)-3-(3-dimethylamino-1-hydroxy-1,2-dimethylpropyl)-phenolhydrochloride(+17)

The enantiomers (−17) and (+17) were prepared under the conditions cited in Example 2.

(−17): yield: 82% theoretical m.p.: 204–205° C.

$[\alpha]_{D\ RT} = -42.0°$ (c=0.94; methanol)

(+17): yield: 83% theoretical m.p.: 204–205° C.

$[\alpha]_{D\ RT} = +41.2°$ (c=1.01; methanol)

Example 22

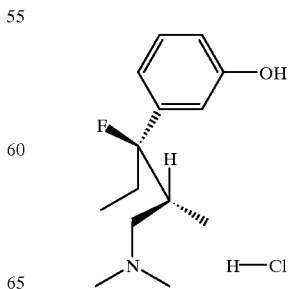

(+)-(1R,2R)-3-(3-dimethylamino-1-ethyl-1-fluoro-2-methylpropyl)-phenol hydrochloride(+18)

1st Step

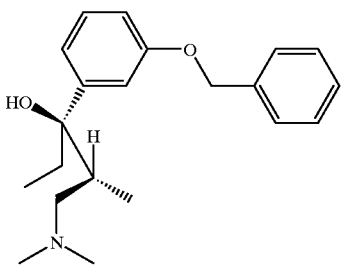

(+)-(1R,2R)-3-(3-benzyloxyphenyl)-1-dimethylamino-2-methylpentan-3-ol (+19)

The base was released with dichloromethane/sodium hydroxide solution from enantiomer (+16) obtained as in Example 19, and dichloromethane was removed by distillation after drying the solution. 5.3 g (22 mmole) of base were dissolved in 27 ml of dry dimethylformamide and added in several portions to 1.2 g of 50% sodium hydride. After the addition of 2.8 ml (24 mmole) benzoyl chloride the mixture was heated for three hours at 70° C. The reaction mixture was then cooled to room temperature and poured on to an ice/water mixture. It was extracted three times with 70 ml ether in each case. After drying the combined organic phases over sodium sulphate, the solvent was distilled off and the residue was introduced on to a 4.5×30 cm column packed with silica gel. 6.8 g of base (+19) (92% theoretical) were obtained as a light yellow, highly viscous oil by elution with diisopropyl ether/methanol.

2nd Step

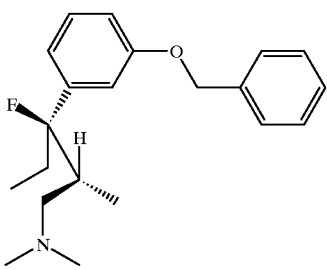

(+)-(2R,3R)-[3-(3-benzyloxyphenyl)-3-fluoro-2-methylpentyl]-dimethylamine(+20)

6.8 g (21 mmole) of (+19), dissolved in 80 ml dichloromethane, were added drop-wise at −20° C. to a solution of 3.7 g (23 mmole) diethylaminosulphur trifluoride in 30 ml of dry dichloromethane. After the addition was complete, the mixture was stirred for 30 minutes at this temperature and then warmed to room temperature. After stirring for a further one hour at room temperature, the mixture was cooled to 0–5° C. and hydrolysed with 50 ml water. After phase separation, the aqueous phase was extracted twice with 50 ml dichloromethane. The combined organic phases were dried and freed from solvent by distillation under vacuum. The crude mixture obtained (8.04 g) was introduced on to a 6×50 cm column packed with silica gel and eluted with 1:1 ethyl acetate/methanol. 3.04 g of base (+20) (40% theoretical) were obtained as a light yellow, viscous oil.

3rd Step

(+)-(1R,2R)-3-(3-dimethylamino-1-ethyl-1-fluoro-2-methylpropyl)-phenol hydrochloride(+18)

3.0 g (91 mmole) of (+20) were dissolved in 15 ml of dry methanol and added to 0.44 g palladium on activated carbon (10% Pd) in a hydrogenation apparatus. 215 ml hydrogen was consumed after stirring for three hours at room temperature. The catalyst was removed by filtration, and the methanol was removed by distillation. 2.22 g of base were obtained, from which 2.0 g of hydrochloride (+18) (79% theoretical) were obtained with trimethylchlorosilane/water in 2-butanone.

m.p.: 174–176° C.

$[\alpha]_{D\ RT} = +29.5°$ (c=1.08; methanol)

Example 23

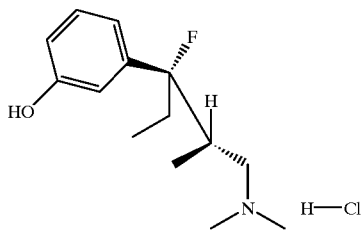

(−)-(1S,2S)-3-(3-dimethylamino-1ethyl-1-fluoro-2-methylpropyl)-phenol hydrochloride(−18)

Enantiomer (−18) was obtained in a yield of 29% theoretical from enantiomer (−16) obtained as in Example 19, under the conditions cited in Example 22.

m.p.: 170–172° C.

$[\alpha]_{D\ RT} = -28.4°$ (c=1.03; methanol)

Example 24

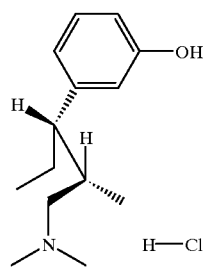

(+)-(1S,2R)-3-(3-dimethylamino-1-ethyl-2-methylpropyl)-phenol hydrochloride(+21)

1st Step

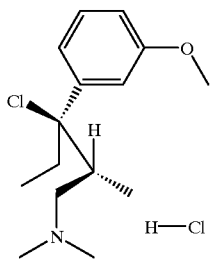

(+)-(2R,3R)-[3-chloro-3-(-3-methoxyphenyl)-2-methylpentyl]-dimethylamine hydrochloride(+22)

10 g (35 mmole) of (+1), prepared as in Example 2, were added to 10 ml thionyl chloride at room temperature. Nitrogen was subsequently passed over the reaction mixture for two hours to remove excess thionyl chloride. After a fresh addition of 10 ml thionyl chloride the reaction mixture was allowed to stand for 12 hours before excess thionyl chloride was again removed over a period of 2.5 hours by means of a stream of nitrogen. After drying, the residue was dissolved in 10 ml of ice-cold 2-butanone and mixed with stirring with 200 ml ether and then with 140 ml diisopropyl ether. The supernatant solvent phase was decanted off and the remaining oil was again taken up in 10 ml 2-butanone. After the addition of seed crystals, 300 ml diisopropyl ether were added drop-wise with vigorous stiring over three hours, whereupon the hydrochloride crystallised out. 9.8 g of (22) (91% theoretical) were obtained.

m.p.: 120° C. (decomposition)

$[\alpha]_{D\ RT}$=+24.70° (c=1.01; methanol)

2nd Step

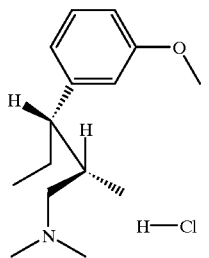

(+)-(2R,3R)-[3-(3-methoxyphenyl)-2-methylpentyl]-dimethylamine hydrochloride(+23)

46 g of dried zinc chloride were dissolved in 580 ml of dry ether and subsequently added drop-wise to a slurry of 31 g sodium borohydride in 1800 ml ether. After stirring for 12 hours, 500 ml were removed by decantation from the zinc borohydride suspension obtained and added drop-wise to 9.8 g (32 mmole) of (+22) in 200 ml of dry ether. The reaction mixture was stirred for 72 hours at room temperature and then added drop-wise to 40 ml of a saturated ammonium chloride solution with cooling in an ice bath. After phase separation, the ether phase was washed twice with saturated brine; after drying over sodium sulphate the solvent was distilled off under vacuum. 7.3 g of an amine-borane complex were obtained, which were dissolved in 100 ml of dry methanol to isolate the free base. After the addition of 7.5 g triphenylphosphine the mixture was heated for 18 hours under reflux. After removing the solvent by distillation the residue was added to 100 ml of 5% hydrochloric acid, and the hydrochloric acid phase was subsequently washed twice with 50 ml ether. Thereafter the hydrochloric acid phase was made alkaline with concentrated sodium hydroxide solution whilst cooling in an ice bath, and was solvent-extracted twice with 50 ml dichloromethane. After drying the combined organic phases over sodium sulphate the solvent was distilled off under vacuum and the remaining residue (5.2 g) was taken up in 2-butanone. After the addition of trimethylchlorosilane/water, 4.3 g of hydrochloride (+23) (50% theoretical) crystallised out.

m.p.: 163–164° C.

$[\alpha]_{D\ RT}$=+25.2° (c=0.95; methanol)

3rd Step (+)-(1R,2R)-3-(3-dimethylamino-1-ethyl-2-methylpropyl)-phenol hydrochloride(+21)

4.3 g (15 mmole) of (+23) from step 2 were added to 100 ml of concentrated hydrobromic acid. The mixture was then heated under reflux for two hours. After cooling to room temperature the reaction mixture was concentrated under the vacuum from a water pump. The residue was treated with concentrated sodium hydrogen carbonate solution until an alkaline reaction was obtained. After extracting twice with 50 ml dichloromethane in each case the combined organic phases were dried over sodium sulphate. Dichloromethane was then distilled off under vacuum and the residue (4 g) was taken up in 2-butanone. After the addition of trimethylchlorosilane/water, 3.8 g of hydrochloride (+21) (98% theoretical) crystallised out.

m.p.: 194–196° C.

$[\alpha]_{D\ RT}$=+24.50 (c=1.10; methanol)

Example 25

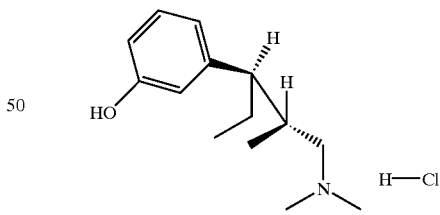

(−)-(1S,2S)-3-(3dimethylamino-1-ethyl-2-methylpropyl)-phenol hydrochloride(−21)

Enantiomer (−21) was obtained in 45% yield under the conditions cited in Example 24 from (−1), which was prepared as in Example 2.

m.p.: 168–170° C.

$[\alpha]_{D\ RT}$=−27.5° (c=0.97; methanol)

Example 26

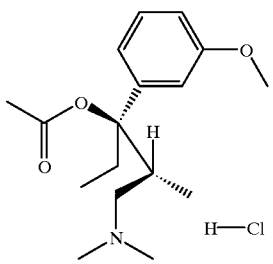

(+)-(1R,2R)-acetic acid-3-dimethylamino-1-ethyl-1-(3-methyoxyphenyl)-2-methyl-propyl ester hydrochloride(+24)

The base was released from enantiomer (+1), which was prepared as in Example 2, with dichloromethane/sodium hydroxide solution. After drying the solution, dichloromethane was removed by distillation. 3.0 g (39 mmole) acetyl chloride were added drop-wise, whilst cooling in an ice bath, to 10 g (35 mmole) of the base obtained, which had been taken up in 150 ml of dry dichloromethane. After the addition of acetyl chloride was complete, the reaction mixture was warmed to room temperature, and after stirring for two hours was mixed with 100 ml of saturated sodium hydrogen carbonate solution. The organic phase was separated from the aqueous phase and the aqueous phase was extracted twice with 50 ml dichloromethane. The organic phases were combined and dried over sodium sulphate. After removing the solvent by distillation, 13.4 g crude mixture were obtained, from which 10.7 g of hydrochloride (+24) (93% theoretical) was obtained with trimethylchlorosilane/water in 2-butanone/ethyl acetate.

m.p.: 153° C.

$[\alpha]_{D\ RT} = -17.3°$ (c=1.04; methanol)

Example 27

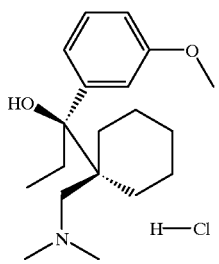

(1RS)-1-(1-dimethylaminomethyl-cyclohexyl)-1-(3-methoxyphenyl)-propan-1-ol hydrochloride(25)

1st Step

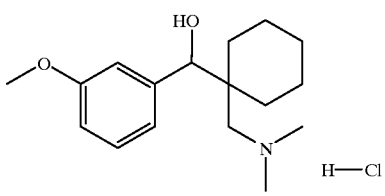

(1RS)-1-(1-dimethylaminomethyl-cyclohexyl)-(3-methoxyphenyl)-methanol hydrochloride(26)

44 g crude mixture was obtained from 25 g (150 mmole) 1-dimethylaminomethyl-cyclohexane carbaldehyde, 32.9 g (180 mmole) 1-bromo-3-methoxybenzene and 4.3 g (180 mmole) magnesium turnings, under the conditions cited in Example 1. This mixture was introduced on to a 7×40 cm column packed with silica gel and eluted with 4:1 diisopropyl ether/methanol. 38 g of base were obtained, from which 40 g of hydrochloride (26) (85% theoretical) with a melting point of 235° C. were obtained with trimethylchlorosilane/water in 2-butanone.

2nd Step

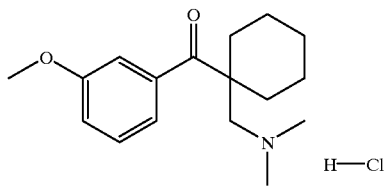

(1RS)-(1-dimethylaminomethyl-cyclohexyl)-(3-methoxyphenyl)-methanone hydrochloride(27)

The base was released from (26) with dichloromethane/sodium hydroxide solution and after drying the solution dichloromethane was removed by distillation. 8.3 g (30 mmole) of base were dissolved in 30 ml n-hexane and added drow-wise to a suspension consisting of 95 g pyridinium chlorochromate (prepared according to Synthesis 1980, 223) absorbed on neutral alumina. After stirring for 72 hours at room temperature the reaction mixture was mixed with 120 ml dichloromethane, stirred for a further 2 hours and then filtered through 30 g alumina. The filter residue was washed three times by decantation with 50 ml dichloromethane and ether in each case. The organic phases were combined with the filtrate and freed from solvent by distillation. The residue obtained was taken up in 60 ml of 2 Normal sodium hydroxide solution and extracted four times with 20 mg ethyl acetate in each case. After drying the combined organic phases, the solvent was removed by distillation. 4.8 g crude mixture were obtained, which was introduced on to a 6×30 cm column packed with silica gel and eluted, firstly with ethyl acetate, then with 9:1 ethyl acetate/methanol and finally with 4:1 ethyl acetate/methanol. 3.8 g of base were obtained, from which 3.1 g of hydrochloride (27) (33% theoretical) with a melting point of 174° C. were obtained with trichlorosilane/water in 2-butanone.

3rd Step (1RS)-1-(1-dimethylaminomethyl-cyclohexyl)-1-(3-methoxyphenyl)-propan-1-ol hydrochloride(25)

3.0 g crude mixture was obtained, under the conditions cited in Example 1, from 2.8 g (10 mmole) of (27) in the form of the base, 1.4 g (13 mmole) bromoethane and 0.32 g (13 mmole) magnesium turnings, using ether as the solvent. This mixture was introduced on to a 3×20 cm column packed with silica gel and eluted with 19:1 diisopropyl ether/methanol. 2.1 g of base were obtained, from which 1.9 g of hydrochloride (25) (55% theoretical) with a melting point of 230° C. were obtained with trichlorosilane/water in 2-butanone/ethyl acetate.

Example 28

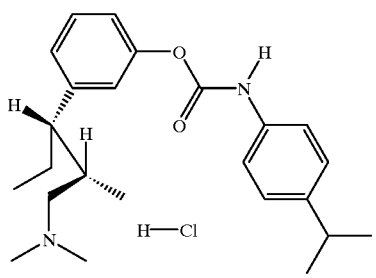

(−)-(2R,3S)-{3[3-(p-isopropyl-phenyl-carbamoyl)-
oxy-phenyl]-2-methylpentyl-dimethylamine
hydrochloride(−28)

The base was released from enantiomer (+21), which was prepared as in Example 24, with dichloromethane/sodium hydroxide solution, and after drying the solution dichloromethane was removed by distillation. 2.2 g (10 mmole) of the base obtained were dissolved in 20 ml of dry toluene and mixed with 1.8 g (11 mmole) 4-isopropylphenyl isocyanate. After stirring for 20 hours at room temperature the toluene was removed by distillation. The residue was reacted with trimethylchlorosilane/water in n-propyl acetate to form 3.2 g of hydrochloride (−28) (76% theoretical).

m.p.: 151–152° C.

$[\alpha]_D{}^{RT} = -5.2°$ (c=1.11; methanol)

Pharmacological Investigations

Writhing Test on Mice

The analgesic effectiveness of the compounds according to the invention was investigated in the phenylquinone-induced writhing test, modified according to I.C. Hendershot, J. Forsaith in *J. Pharmacol. Exptl. Ther.* 125, 237 (1959), on mice. Male NMRI mice with a weight between 25 and 30 g were used for this purpose. For each dose of substance, each 10 animals received, 30 minutes after the oral administration of a compound according to the invention, 0.3 ml per mouse of an 0.02% aqueous phenylquinone solution (phenylbenzoquinone manufactured by Sigma, Deisenhofen; solution prepared with the addition of 5% ethanol and kept on a water bath at 45° C.) administered intraperitoneally. Thereafter the animals were placed individually in observation cages. The number of pain-induced stretching movements (writhing reaction=straightening of the body with stretching of the rear extremities) was counted with the aid of a push-button counter. The $ED_{50}$ value (effective dose with 50% inhibition of writhing reaction) was calculated with a 95% confidence limit by means of regression analysis (evaluation program supplied by Martens EDV-Service, Eckental) from the dose-dependent decrease in the writhing reaction, by comparison with mice tested in parallel to which only phenylquinone had been administered. All the compounds according to the invention which were investigated exhibited a pronounced analgesic effect. The results are summarized in the following Table:

TABLE

Writhing inhibition

| Example | Compound according to the invention | $ED_{50}$ [mg/kg per os] | % Inhibition 25 mg/kg per os |
|---|---|---|---|
| 1 | (1) | 5.8 | |
| 2 | (−1) | 22.3 | |
| 2 | (+1) | 1.1 | |
| 3 | (2) | 13.2 | |
| 4 | (3) | | −81.3 |
| 5 | (4) | 15.5 | |
| 6 | (5) | 8.3 | |
| 7 | (6) | 11.8 | |
| 8 | (7) | 27.3 | |
| 9 | (8) | 12.9 | |
| 10 | (9) | 12.8 | |
| 11 | (10) | 12.9 | |
| 13 | (12) | 19.9 | |
| 15 | (14) | 10.5 | |
| 16 | (15) | 3.8 | |
| 17 | (+15) | | −95.2 |
| 18 | (16) | | −100.0 |
| 19 | (−16) | 16.1 | |
| 19 | (+16) | 1.0 | |
| 20 | (17) | | −87.0 |
| 21 | (−17) | | −58.3 |
| 21 | (+17) | | −97.2 |
| 22 | (+18) | 15.7 | |
| 24 | (+21) | 1.9 | |

The foregoing description and examples have been set forth merely to illustrate the invention and are not intended to be limiting. Since modifications of the disclosed embodiments incorporating the spirit and substance of the invention may occur to persons skilled in the art, the invention should be construed to include all variations within the scope of the appended claims and equivalents thereof.

What is claimed is:

1. A method of preparing a 1-phenyl-3-dimethylaminopropane compound corresponding to formula

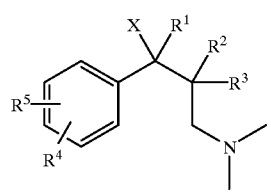

I wherein
X represents OH, F, Cl, H or an $OCOR^6$ group in which $R^6$ is a $C_{1-3}$-alkyl group;
$R^1$ is a $C_{1-4}$-alkyl group;
$R^2$ represents H or a $C_{1-4}$-alkyl group, and $R^3$ represents H or a straight chain $C_{1-4}$-alkyl group, or $R^2$ and $R^3$ together form a $C_{4-7}$ cycloalkyl radical;
when $R^5$ represents H, $R^4$ represents:
(A) meta-O—Z, wherein Z is H, $C_{1-3}$-alkyl, $PO(OC_{1-4}alkyl)_2$, $CO(OC_{1-5}$-alkyl), $CONH$—$C_6H_4$—$(C_{1-3}$-alkyl) or $CO$—$C_6H_4$—$R^7$, in which $R^7$ is ortho-$OCOC_{1-3}$-alkyl or meta- or para-$CH_2N(R^8)_2$, where $R^8$ is $C_{1-4}$-alkyl or 4-morpholino, or
(B) meta-S—$C_{1-3}$-alkyl, meta-Cl, meta-F, meta-$CR^9R^{10}R^{11}$, ortho-OH, ortho-O—$C_{2-3}$-alkyl, para-F or para-$CR^9R^{10}R^{11}$, where $R^9$, $R^{10}$ and $R^{11}$ independently represent H or F;
when $R^5$ represents para-Cl, para-F, para-OH or para-O—$C_{1-3}$-alkyl, $R^4$ represents meta-Cl, meta-F, meta-OH or meta-O—$C_{1-3}$-alkyl; or $R^4$ and $R^5$ together represent 3,4-OCH=CH— or 3,4-OCH=CHO—, as diastereoisomers or enantiomers in the form of free bases;

said method comprising:
(1) reacting a compound of formula I in which X represents Cl with at least one substance selected from the group consisting of zinc borohydride, zinc cyanoborohydride and tin cyanoborohydride to form a final compound in which X represents H;
(2) reacting a compound of formula I in which X represents OH with dimethylaminosulfur trifluoride in a solvent to form a final compound in which X represents F;
(3) reacting a compound of formula I in which X represents OH with thionyl chloride to form a final product in which X represent Cl;
(4) reacting a compound of formula I in which X represents OH or with an acid chloride Cl—COOR$^6$ to form a final compound in which X represents OCOR$^6$; or
(5) reacting a β-dimethylaminoketone of formula II

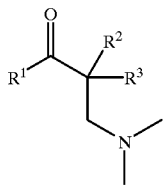

II with an organometallic compound of formula III

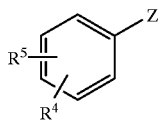

III in which Z represents MgCl, MgBr, MgI or Li to form a final compound in which X represent OH; and optionally converting a free base into a salt with a physiologically acceptable acid.

2. A method according to claim 1, wherein
X represents OH, F, Cl or H;
$R^1$ represents a $C_{1-4}$-alkyl group;
$R^2$ represents H or $CH_3$;
$R^3$ represents H or $CH_3$, and
$R^5$ represents H, and $R^4$ represents meta-$OC_{1-3}$-alkyl, meta-OH, meta-S—$C_{1-3}$-alkyl, meta-F, meta-Cl, meta-$CH_3$, meta-$CF_2H$, meta-$CF_3$ or para-$CF_3$, or
$R^5$ represents para-Cl or para-F, and $R^4$ represents meta-Cl or meta-F, or
$R^4$ and $R^5$ together represent 3,4-OCH=CH—.

3. A method according to claim 1, wherein $R^2$ and $R^3$ have different meanings, and wherein said compound is a diastereoisomer having the configuration Ia

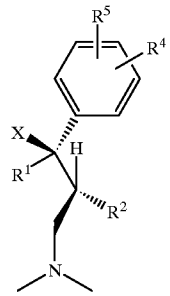

Ia

4. A method according to claim 1, in which X represents OH, said method comprising reacting a β-dimethylaminoketone of formula II

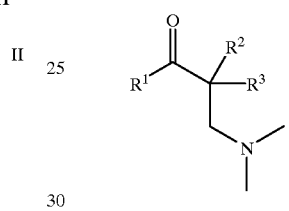

II with an organometallic compound of formula III

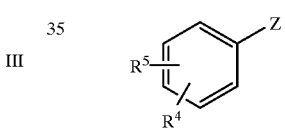

III in which Z represents MgCl, MgBr, MgI or Li.

5. A method according to claim 1, in which X represents H, said method comprising reacting a compound of formula I in which X represents Cl with at least one substance selected from the group consisting of zinc borohydride, zinc cyanoborohydride and tin cyanoborohydride.

6. A method according to claim 1, in which X represents F, said method comprising reacting a compound of formula I in which X represents OH with dimethylaminosulfur trifluoride in a solvent.

7. A method according to claim 1, in which X represents Cl, said method comprising reacting a compound of formula I in which X represents OH with thionyl chloride.

8. A method according to claim 1, in which X represents an OCOR$^6$ group in which R$^6$ is $C_{1-3}$-alkyl group, said method comprising reacting a compound of formula I in which X represents OH with an acid chloride Cl—COOR$^6$.

* * * * *

UNITED STATES PATENT AND TRADEMARK OFFICE
CERTIFICATE OF CORRECTION

PATENT NO. : 6,344,558 B1  Page 1 of 1
DATED : February 5, 2002
INVENTOR(S) : Helmut Buschmann et al.

It is certified that error appears in the above-identified patent and that said Letters Patent is hereby corrected as shown below:

<u>Title page,</u>
Item [73], please correct the spelling of the Assignee to read -- Gruenenthal GmbH, Aachen (DE) --

Signed and Sealed this

Twenty-seventh Day of August, 2002

*Attest:*

JAMES E. ROGAN
*Attesting Officer*      *Director of the United States Patent and Trademark Office*